(12) United States Patent
Sartor et al.

(10) Patent No.: US 9,445,865 B2
(45) Date of Patent: Sep. 20, 2016

(54) ELECTROSURGICAL INSTRUMENT WITH END-EFFECTOR ASSEMBLY INCLUDING ELECTRICALLY-CONDUCTIVE, TISSUE-ENGAGING SURFACES AND SWITCHABLE BIPOLAR ELECTRODES

(71) Applicant: COVIDIEN LP, Mansfield, MA (US)

(72) Inventors: Joe D. Sartor, Longmont, CO (US); Daniel Friedrichs, Aurora, CO (US)

(73) Assignee: COVIDIEN LP, Mansfield, MA (US)

( * ) Notice: Subject to any disclaimer, the term of this patent is extended or adjusted under 35 U.S.C. 154(b) by 121 days.

(21) Appl. No.: 14/295,730

(22) Filed: Jun. 4, 2014

(65) Prior Publication Data

US 2015/0080880 A1 Mar. 19, 2015

Related U.S. Application Data

(60) Provisional application No. 61/878,145, filed on Sep. 16, 2013.

(51) Int. Cl.
*A61B 18/18* (2006.01)
*A61B 18/14* (2006.01)
(Continued)

(52) U.S. Cl.
CPC ....... *A61B 18/1445* (2013.01); *A61B 18/1206* (2013.01); *A61B 2018/0063* (2013.01); *A61B 2018/00922* (2013.01); *A61B 2018/126* (2013.01)

(58) Field of Classification Search
CPC .......... A61B 18/1206; A61B 18/1445; A61B 2018/0063; A61B 2018/00922; A61B 2018/126

USPC ...................................................... 606/45–52
See application file for complete search history.

(56) References Cited

U.S. PATENT DOCUMENTS

D249,549 S 9/1978 Pike
D263,020 S 2/1982 Rau, III
(Continued)

FOREIGN PATENT DOCUMENTS

CN 201299462 9/2009
DE 2415263 A1 10/1975
(Continued)

OTHER PUBLICATIONS

U.S. Appl. No. 13/731,674, filed Dec. 31, 2012; inventor: Siebrecht.
(Continued)

*Primary Examiner* — Michael Peffley
*Assistant Examiner* — Amanda Zink

(57) ABSTRACT

An electrosurgical instrument includes a housing, an elongated shaft, and an end-effector assembly. The proximal end of the shaft is operably associated with the housing. The end-effector assembly is operably coupled to the distal end of the shaft and includes first and second jaw members. Each of the first and second jaw members includes a sealing plate and a bipolar electrode. Either one or both of the first and second jaw members is movable from a position in spaced relation relative to the other jaw member to at least one subsequent position wherein the sealing plates cooperate to grasp tissue therebetween. The electrosurgical instrument includes a semiconductor switch operably coupled to at least one of the sealing plates and at least one of the bipolar electrodes. The semiconductor switch is configured to enable user selection between energizing the at least one sealing plate or the at least one bipolar electrode.

18 Claims, 6 Drawing Sheets

(51) Int. Cl.
*A61B 18/12* (2006.01)
*A61B 18/00* (2006.01)

(56) References Cited

U.S. PATENT DOCUMENTS

| | | | |
|---|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| 6,562,037 B2 | 5/2003 | Paton et al. |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al |
| D545,432 S | 6/2007 | Watanabe |
| D547,154 S | 7/2007 | Lee et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| 7,431,721 B2 | 10/2008 | Paton et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 7,780,662 B2 | 8/2010 | Bahney |
| D627,462 S | 11/2010 | Kingsley |
| D628,289 S | 11/2010 | Romero |
| D628,290 S | 11/2010 | Romero |
| D630,324 S | 1/2011 | Reschke |
| 7,931,649 B2 | 4/2011 | Couture et al. |
| D649,249 S | 11/2011 | Guerra |
| D649,643 S | 11/2011 | Allen, IV et al. |
| 8,147,485 B2 | 4/2012 | Wham et al. |
| D661,394 S | 6/2012 | Romero et al. |
| D670,808 S | 11/2012 | Moua et al. |
| 8,333,765 B2 | 12/2012 | Johnson et al. |
| 8,348,948 B2 | 1/2013 | Bahney |
| D680,220 S | 4/2013 | Rachlin |
| 8,597,297 B2 | 12/2013 | Couture et al. |
| 2007/0093801 A1* | 4/2007 | Behnke .......... A61B 18/1233 606/34 |
| 2007/0265616 A1 | 11/2007 | Couture et al. |
| 2008/0249523 A1* | 10/2008 | McPherson ...... A61B 18/1445 606/41 |
| 2009/0234354 A1 | 9/2009 | Johnson et al. |
| 2011/0282339 A1* | 11/2011 | Weizman ......... A61B 18/1445 606/33 |
| 2012/0172873 A1 | 7/2012 | Artale et al. |
| 2012/0253344 A1* | 10/2012 | Dumbauld ....... A61B 18/1445 606/52 |
| 2012/0310241 A1 | 12/2012 | Orszulak |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |

(56) References Cited

FOREIGN PATENT DOCUMENTS

| | | |
|---|---|---|
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2008-054926 A | 3/2008 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02045589 A3 | 9/2002 |
| WO | 2006/021269 A1 | 3/2006 |
| WO | 2005110264 A3 | 4/2006 |
| WO | 2008/040483 A1 | 4/2008 |
| WO | 2011/018154 A1 | 2/2011 |

OTHER PUBLICATIONS

U.S. Appl. No. 14/065,644, filed Oct. 29, 2013; inventor: Reschke.
U.S. Appl. No. 14/098,953, filed Dec. 6, 2013; inventor: Cunningham.
U.S. Appl. No. 14/100,237, filed Dec. 9, 2013; inventor: Reschke.
U.S. Appl. No. 14/103,971, filed Dec. 12, 2013; inventor: Roy.
U.S. Appl. No. 14/105,374, filed Dec. 13, 2013; inventor: Moua.
U.S. Appl. No. 14/152,618, filed Jan. 10, 2014; inventor: Artale.
U.S. Appl. No. 14/152,690, filed Jan. 10, 2014; inventor: Hart.
U.S. Appl. No. 14/169,358, filed Jan. 31, 2014; inventor: Reschke.
U.S. Appl. No. 14/173,391, filed Feb. 5, 2014; inventor: Kharin.
U.S. Appl. No. 14/176,341, filed Feb. 10, 2014; inventor: Hart.
U.S. Appl. No. 14/177,812, filed Feb. 11, 2014; inventor: Dycus.
U.S. Appl. No. 14/182,894, filed Feb. 18, 2014; inventor: Hart.
U.S. Appl. No. 14/182,967, filed Feb. 18, 2014; inventor: Latimer.
U.S. Appl. No. 14/183,090, filed Feb. 18, 2014; inventor: Arts.
U.S. Appl. No. 14/196,066, filed Mar. 4, 2014; inventor: McCullough.
U.S. Appl. No. 14/250,180, filed Apr. 10, 2014; inventor: Guerra.
U.S. Appl. No. 14/253,017, filed Apr. 15, 2014; inventor: Orszulak.
U.S. Appl. No. 14/260,905, filed Apr. 24, 2014; inventor: Jensen.
U.S. Appl. No. 14/268,051, filed May 2, 2014; inventor: Hart.
U.S. Appl. No. 14/268,140, filed May 2, 2014; inventor: Twomey.
U.S. Appl. No. 14/273,350, filed May 8, 2014; inventor: Gilbert.
U.S. Appl. No. 14/274,445; filed May 9, 2014; inventor: Hixson.
U.S. Appl. No. 14/276,465, filed May 13, 2014; inventor: Kappus.
U.S. Appl. No. 14/282,738, filed May 20, 2014; inventor: Rachlin.
U.S. Appl. No. 14/284,618, filed May 22, 2014; inventor: Hempstead.
U.S. Appl. No. 14/286,105, filed May 23, 2014; inventor: Johnson.
U.S. Appl. No. 14/294,316, filed Jun. 3, 2014; inventor: Johnson.
U.S. Appl. No. 14/295,049, filed Jun. 3, 2014; inventor: Couture.
U.S. Appl. No. 14/295,730, filed Jun. 4, 2014; inventor: Sartor.
U.S. Appl. No. 14/295,757, filed Jun. 4, 2014; inventor: McKenna.
U.S. Appl. No. 14/297,316, filed Jun. 5, 2014; inventor: Ackley.
U.S. Appl. No. 14/297,404, filed Jun. 5, 2014; inventor: Allen.
U.S. Appl. No. 14/299,740, filed Jun. 9, 2014; inventor: Larson.
U.S. Appl. No. 14/319,869, filed Jun. 30, 2014; inventor: Cunningham.
U.S. Appl. No. 14/322,513, filed Jul. 2, 2014; inventor: Duffin.
U.S. Appl. No. 14/335,303, filed Jul. 18, 2014; inventor: Lee.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With The LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003.

(56) References Cited

OTHER PUBLICATIONS

"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulembah et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. " Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
U.S. Appl. No. 08/926,869, filed Sep. 10, 1997; inventor: James G. Chandler.
U.S. Appl. No. 09/177,950, filed Oct. 23, 1998; inventor: Randel A. Frazier.
U.S. Appl. No. 09/387,883; filed Sep. 1, 1999; inventor: Dale F. Schmaltz.
U.S. Appl. No. 09/591,328, filed Jun. 9, 2000; inventor: Thomas P. Ryan.
U.S. Appl. No. 12/336,970; filed Dec. 17, 2008; inventor: Paul R. Sremeich.

\* cited by examiner

ELECTROSURGICAL INSTRUMENT WITH END-EFFECTOR ASSEMBLY INCLUDING ELECTRICALLY-CONDUCTIVE, TISSUE-ENGAGING SURFACES AND SWITCHABLE BIPOLAR ELECTRODES

CROSS REFERENCE TO RELATED APPLICATION

The present application claims the benefit of and priority to U.S. Provisional Application Ser. No. 61/878,145, filed on Sep. 16, 2013, the entire contents of which are incorporated herein by reference.

BACKGROUND

1. Technical Field

The present disclosure relates to electrosurgical instruments. More particularly, the present disclosure relates to electrosurgical instruments that include an end-effector assembly including electrically-conductive, tissue-engaging surfaces and switchable bipolar electrodes for treating tissue.

2. Discussion of Related Art

Electrosurgical instruments have become widely used by surgeons. Electrosurgery involves the application of thermal and/or electrical energy to cut, dissect, ablate, coagulate, cauterize, seal or otherwise treat biological tissue during a surgical procedure. Electrosurgery is typically performed using an electrosurgical generator operable to output energy and a handpiece including a surgical instrument (e.g., end effector) adapted to transmit energy to a tissue site during electrosurgical procedures. Electrosurgery can be performed using either a monopolar or a bipolar instrument.

The basic purpose of both monopolar and bipolar electrosurgery is to produce heat to achieve the desired tissue/clinical effect. In monopolar electrosurgery, devices use an instrument with a single, active electrode to deliver energy from an electrosurgical generator to tissue, and a patient return electrode or pad that is attached externally to the patient (e.g., a plate positioned on the patient's thigh or back) as the means to complete the electrical circuit between the electrosurgical generator and the patient. When the electrosurgical energy is applied, the energy travels from the active electrode, to the surgical site, through the patient and to the return electrode. In bipolar electrosurgery, both the active electrode and return electrode functions are performed at the site of surgery. Bipolar electrosurgical devices include two electrodes that are located in proximity to one another for the application of current between their surfaces. Bipolar electrosurgical current travels from one electrode, through the intervening tissue to the other electrode to complete the electrical circuit. Bipolar instruments generally include end-effectors, such as grippers, cutters, forceps, dissectors and the like.

Forceps utilize mechanical action to constrict, grasp, dissect and/or clamp tissue. By utilizing an electrosurgical forceps, a surgeon can utilize both mechanical clamping action and electrosurgical energy to effect hemostasis by heating the tissue and blood vessels to cauterize, coagulate/desiccate, seal and/or divide tissue. Bipolar electrosurgical forceps utilize two generally opposing electrodes that are operably associated with the inner opposing surfaces of end effectors and that are both electrically coupled to an electrosurgical generator. In bipolar forceps, the end-effector assembly generally includes opposing jaw assemblies pivotably mounted with respect to one another. In a bipolar configuration, only the tissue grasped between the jaw assemblies is included in the electrical circuit. Because the return function is performed by one jaw assembly of the forceps, no patient return electrode is needed.

By utilizing an electrosurgical forceps, a surgeon can cauterize, coagulate/desiccate and/or seal tissue and/or simply reduce or slow bleeding by controlling the intensity, frequency and duration of the electrosurgical energy applied through the jaw assemblies to the tissue. During the sealing process, mechanical factors such as the pressure applied between opposing jaw assemblies and the gap distance between the electrically-conductive, tissue-contacting surfaces (electrodes) of the jaw assemblies play a role in determining the resulting thickness of the sealed tissue and effectiveness of the seal.

A variety of types of end-effector assemblies have been employed for various types of electrosurgery using a variety of types of monopolar and bipolar electrosurgical instruments.

SUMMARY

A continuing need exists for an open or laparoscopic instrument that combines vessel sealing with bipolar spot heating. There is a need for electrosurgical instrument configurations that minimize the length of sets of parallel conductors, e.g., to avoid the risk associated with parasitic capacitance and leakage current. A need exists for electrosurgical instruments configurations allowing for smaller diameter electrical conductors, e.g., wires, which may allow for reduction in the instrument shaft diameter, which, in turn, may allow for smaller incisions, enhanced maneuverability, and/or increased visibility.

According to an aspect of the present disclosure, an electrosurgical instrument is provided. The electrosurgical instrument includes a housing, an elongated shaft, and an end-effector assembly. The elongated shaft includes a distal end and a proximal end. The proximal end of the shaft is operably associated with the housing. The end-effector assembly is operably coupled to the distal end of the shaft and includes first and second jaw members. Each of the first and second jaw members includes an electrically-conductive, tissue-engaging surface and a bipolar electrode. Either one or both of the first and second jaw members is movable from a position in spaced relation relative to the other jaw member to at least one subsequent position wherein the electrically-conductive, tissue-engaging surfaces cooperate to grasp tissue therebetween. The electrosurgical instrument also includes a semiconductor switch operably coupled to at least one of the electrically-conductive, tissue-engaging surfaces and at least one of the bipolar electrodes. The semiconductor switch is configured to enable user selection between energizing the at least one electrically-conductive, tissue-engaging surface or energizing the at least one bipolar electrode.

According to another aspect of the present disclosure, an electrosurgical instrument is provided and includes a housing, an elongated shaft, and an end-effector assembly. The elongated shaft includes a distal end and a proximal end. The proximal end of the shaft is operably associated with the housing. The end-effector assembly is operably coupled to the distal end of the shaft and includes first and second jaw members. The end-effector assembly includes a first jaw member, a second jaw member, a first electrically-conductive, tissue-engaging surface associated with the first jaw member, a second electrically-conductive, tissue-engaging surface associated with the second jaw member, a first bipolar electrode coupled to a distal end of the first jaw member, and a second bipolar electrode coupled to a distal end of the second jaw member. The end-effector assembly also includes a first semiconductor switch operably coupled to the first electrically-conductive, tissue-engaging surface and the first bipolar electrode. The first semiconductor switch is configured to enable user selection between energizing the first electrically-conductive, tissue-engaging surface or energizing the first bipolar electrode.

BRIEF DESCRIPTION OF THE DRAWINGS

Objects and features of the presently-disclosed electrosurgical instruments and end-effector assemblies including electrically-conductive, tissue-engaging surfaces and switchable bipolar electrodes for use in electrosurgical instruments to grasp, seal, and/or divide tissue will become apparent to those of ordinary skill in the art when descriptions of various embodiments thereof are read with reference to the accompanying drawings, of which.

DETAILED DESCRIPTION

Figure 1:
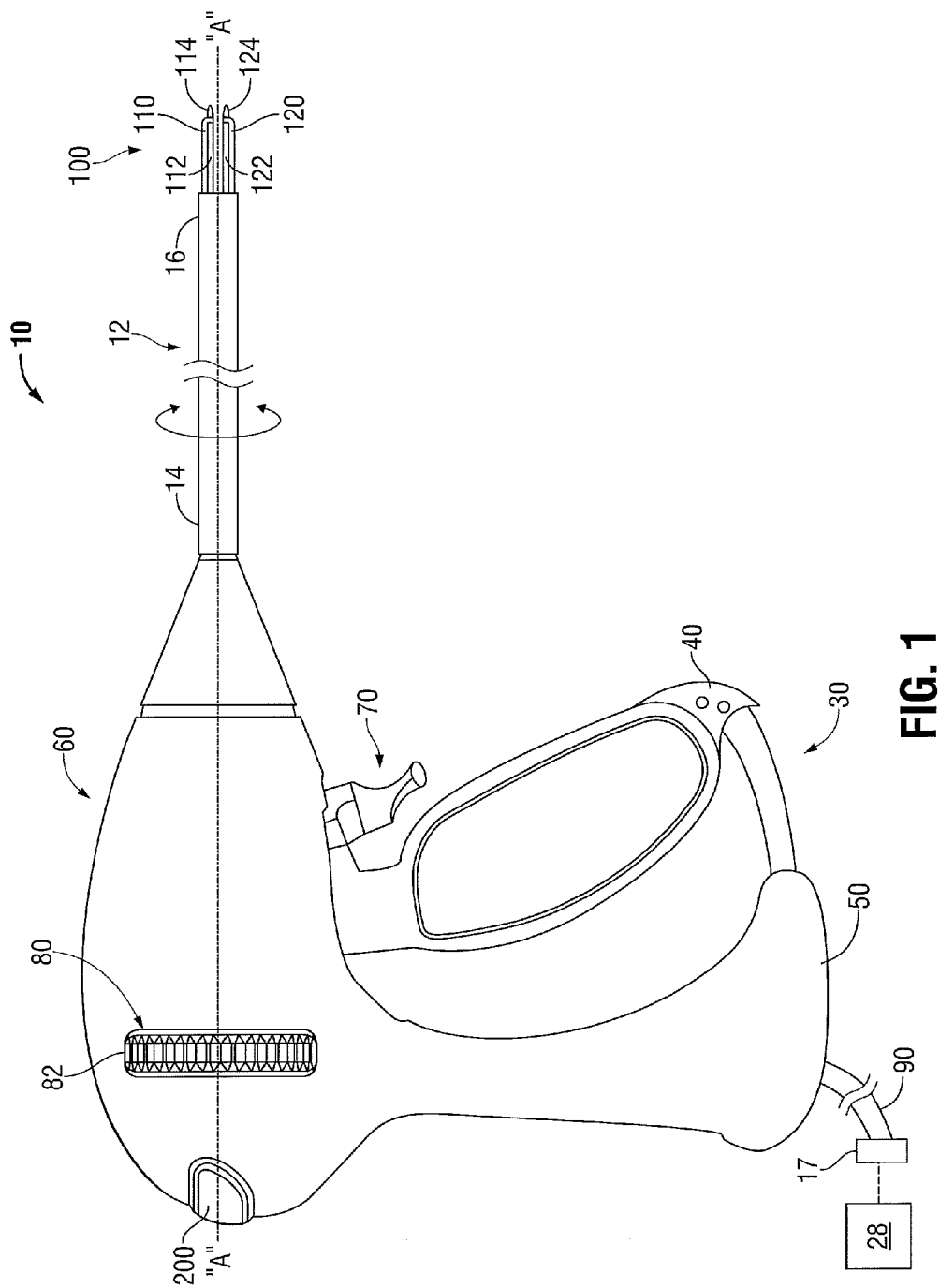
FIG. 1 is a schematic view of an electrosurgical instrument showing a housing, a rotatable member, a shaft, and an end-effector assembly including electrically-conductive, tissue-engaging surfaces and bipolar electrodes in accordance with an embodiment of the present disclosure.

Hereinafter, embodiments of electrosurgical instruments and end-effector assemblies including electrically-conductive, tissue-engaging surfaces, and switchable bipolar electrodes for use in electrosurgical instruments to grasp, seal, and/or divide tissue of the present disclosure are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

This description may use the phrases "in an embodiment," "in embodiments," "in some embodiments," or "in other embodiments," which may each refer to one or more of the same or different embodiments in accordance with the present disclosure.

As it is used in this description, "transmission line" generally refers to any transmission medium that can be used for the propagation of signals from one point to another. As it is used in this description, "switch" or "switches" generally refers to any electrical actuators, mechanical actuators, electro-mechanical actuators (rotatable actuators, pivotable actuators, toggle-like actuators, buttons, etc.), optical actuators, or any suitable device that generally fulfills the purpose of connecting and disconnecting electronic devices, or component thereof, instruments, equipment, transmission lines or connections and appurtenances thereto, or software.

As it is used in this description, "user interface" generally refers to any visual, graphical, tactile, audible, sensory or other mechanism for providing information to and/or receiving information from a user or other entity. The term "user interface" as used herein may refer to an interface between a human user (or operator) and one or more devices to enable communication between the user and the device(s). Examples of user interfaces that may be employed in various embodiments of the present disclosure include without limitation, switches, potentiometers, buttons, dials, sliders, a mouse, keyboard, keypad, joysticks, trackballs, display screens, various types of graphical user interfaces (GUIs), touch screens, microphones and other types of sensors or devices that may receive some form of human-generated stimulus and generate a signal in response thereto.

Various embodiments of the present disclosure provide electrosurgical instruments with an end-effector assembly including electrically-conductive, tissue-engaging surfaces and bipolar electrodes. Embodiments of the presently-disclosed electrosurgical instruments may be suitable for sealing, cauterizing, coagulating/desiccating, and/or cutting vessels and vascular tissue. Embodiments of the presently-disclosed electrosurgical instruments may be suitable for utilization in endoscopic surgical procedures and/or suitable for utilization in open surgical applications. Embodiments of the presently-disclosed electrosurgical instruments may be implemented using electrosurgical energy at radio frequencies (RF) and/or at other frequencies.

The various embodiments disclosed herein may also be configured to work with robotic surgical systems and what is commonly referred to as "Telesurgery." Such systems employ various robotic elements to assist the surgeon in the operating theater and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include, remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. In various embodiments disclosed herein, an end-effector assembly including electrically-conductive, tissue-engaging surfaces and bipolar electrodes may be coupled to a pair of master handles by a controller. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

For the purposes herein, the presently-disclosed electrosurgical instruments (e.g., electrosurgical instrument 10 shown in FIG. 1, electrosurgical instrument 20 shown in FIG. 2, electrosurgical instrument 30 shown in FIG. 3, electrosurgical instrument 40 shown in FIG. 4, and electrosurgical instrument 50 shown in FIG. 5) are described in terms of an endoscopic instrument; however, an open version of the devices may also include the same or similar operating components and features as described below In FIG. 1, an embodiment of an electrosurgical instrument 10 is shown for use with various surgical procedures, e.g., vessel sealing with bipolar spot heating, in accordance with the present disclosure. Electrosurgical instrument 10 includes a housing 60, a handle assembly 30, a rotatable assembly 80, a trigger assembly 70, and an end-effector assembly 100 that mutually cooperate to grasp, seal and/or divide tissue, e.g., tubular vessels and vascular tissue.

End-effector assembly 100 generally includes a pair of opposing jaw members 110 and 120 moveable relative to one another, e.g., pivotably mounted with respect to one another. End-effector assembly 100 may be configured as a bilateral jaw assembly, i.e., both jaw members 110 and 120 move relative to one another. Alternatively, the device 10 may include a unilateral assembly, i.e., the end-effector assembly 100 may include a stationary or fixed jaw member, e.g., 120, mounted in fixed relation to the shaft 12 and a pivoting jaw member, e.g., 110, mounted about a pivot pin (not shown) coupled to the stationary jaw member. Jaw members 110 and 120 (also referred to herein as "first and second jaw members 110 and 120") may be curved at various angles to facilitate manipulation of tissue and/or to provide enhanced line-of-sight for accessing targeted tissues.

First and second jaw members 110 and 120 may be formed from any suitable material or combination of materials by any suitable process, e.g., machining, stamping, electrical discharge machining (EDM), forging, casting, injection molding, metal injection molding (MIM), and/or fineblanking. End-effector assembly 100 may include one or more electrically-insulative bushings to electrically isolate the first jaw member 110 from the second jaw member 120. One or both of the jaw members 110 and 120 may include a longitudinally-oriented slot or knife channel (not shown) configured to permit reciprocation of a knife blade (not shown).

Figure 2:
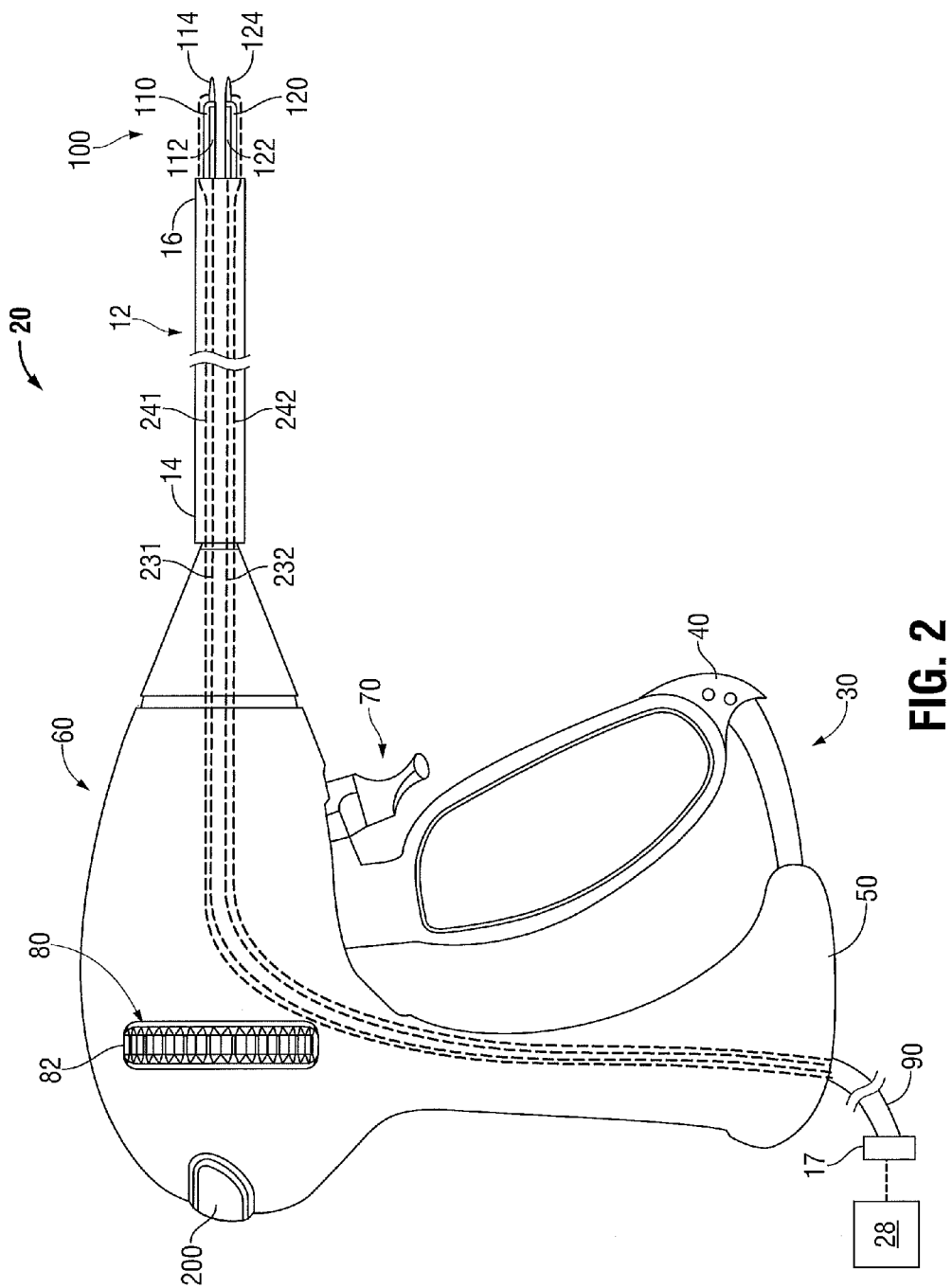
FIG. 2 is a schematic view of an electrosurgical instrument including the end-effector assembly shown in FIG. 1, shown with the electrically-conductive, tissue-engaging surfaces and the bipolar electrodes connected by two pairs of electrical conductors, e.g., wires, to an electrosurgical power generating source in accordance with an embodiment of the present disclosure.
Figure 3:
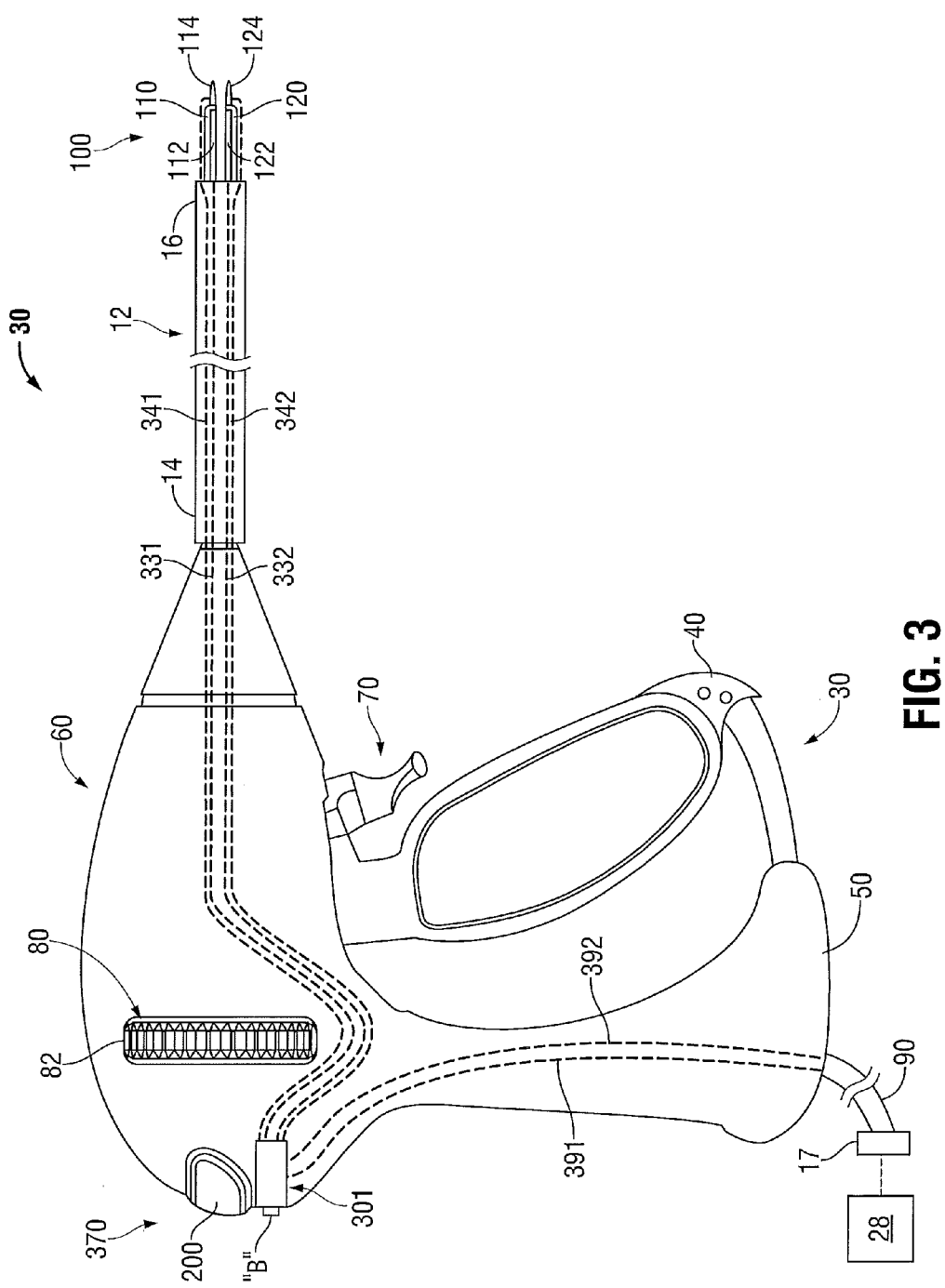
FIG. 3 is a schematic view of an electrosurgical instrument including an end-effector assembly that includes electrically-conductive, tissue-engaging surfaces and bipolar electrodes, and a switch assembly operably coupled thereto, in accordance with the present disclosure.

In some embodiments, as shown in FIGS. 1 through 3, end-effector assembly 100 includes first and second electrically-conductive, tissue-engaging surfaces 112 and 122, respectively, wherein the first electrically-conductive tissue-engaging surface 112 is coupled to, or otherwise disposed in association with, the first jaw member 110, and the second electrically-conductive tissue-engaging surface 122 is coupled to, or otherwise disposed in association with, the second jaw member 120. End-effector assembly 100 may include electrically-insulative bushings configured to electrically isolate, at least in part, the first and second electrically-conductive, tissue-engaging surfaces 112 and 122 (also referred to herein as "first and second sealing plates 112 and 122") from the first and second jaw members 110 and 120, respectively. In some embodiments, the first and second sealing plates 112 and 122 may be integrally formed with the first and second jaw members 110 and 120, respectively. End-effector assembly 100 may be configured wherein either one, or both, of the first and second jaw members 110 and 120 is movable from a position wherein the first and second jaw members 110 and 120 are disposed in spaced relation relative to the other jaw member to at least one subsequent position wherein the first and second sealing plates 112 and 122 cooperate to grasp tissue therebetween.

End-effector assembly 100 includes a first bipolar electrode 114 and a second bipolar electrode 124. First bipolar electrode 114 is coupled to, or otherwise disposed in association with, the first jaw member 110. Second bipolar electrode 124 is coupled to, or otherwise disposed in association with, the second jaw member 120.

End-effector assembly 100 may include a variety of electrically-insulative materials and configurations to provide electrical isolation between each of the first and second sealing plates 112 and 122 and the first and second bipolar electrodes 114 and 124, e.g., to minimize the potential for thermal spread. As can be appreciated, limiting the possibility of thermal spread or the like during an electrosurgical procedure reduces the likelihood of unintentional and/or undesirable collateral damage to surrounding tissue structures which may be adjacent to an intended treatment site. In some embodiments, a configuration of one or more electrically-insulative bushings (not shown) may be associated with either or both the first and second jaw members 110 and 120 to electrically isolate each of the first and second sealing plates 112 and 122 and/or the first and second bipolar electrodes 114 and 124. The first and second bipolar electrodes 114 and 124 may be formed from any suitable material or combination of materials by any suitable process. The shape and size of the first and second bipolar electrodes 114 and 124 may be varied from the configuration depicted in FIGS. 1 through 4.

Electrosurgical instrument 10 generally includes an elongated shaft 12 having a distal end 16 configured to mechanically engage the end-effector assembly 100 and a proximal end 14 configured to mechanically engage the housing 60. End-effector assembly 100 may be selectively and releaseably engageable with the distal end 16 of the shaft 12, and/or the proximal end 14 of the shaft 12 may be selectively and releaseably engageable with the housing 20 and the handle assembly 30. Shaft 12 supports movement of other components therethrough, e.g., to impart movement to the first and second jaw members 110 and 120, respectively.

The proximal end 14 of the shaft 12 is received within the housing 20, and connections relating thereto are disclosed in commonly assigned U.S. Pat. No. 7,150,097 entitled "METHOD OF MANUFACTURING JAW ASSEMBLY FOR VESSEL SEALER AND DIVIDER," commonly assigned U.S. Pat. No. 7,156,846 entitled "VESSEL SEALER AND DIVIDER FOR USE WITH SMALL TROCARS AND CANNULAS," commonly assigned U.S. Pat. No. 7,597,693 entitled "VESSEL SEALER AND DIVIDER FOR USE WITH SMALL TROCARS AND CANNULAS" and commonly assigned U.S. Pat. No. 7,771,425 entitled "VESSEL SEALER AND DIVIDER HAVING A VARIABLE JAW CLAMPING MECHANISM."

Electrosurgical instrument 10 includes an electrosurgical cable 90. Electrosurgical cable 90 may be formed from a suitable flexible, semi-rigid, or rigid cable, and may connect directly to an electrosurgical power generating source 28. In some embodiments, the electrosurgical cable 90 connects the instrument 10 to a connector 17, which further operably connects the instrument 10 to the electrosurgical power generating source 28. Cable 90 may be internally divided into one or more cable leads each of which transmits electrosurgical energy through its respective feed path to the end-effector assembly 100.

Electrosurgical power generating source 28 may be any generator suitable for use with electrosurgical devices, and may be configured to provide various frequencies of electromagnetic energy. Examples of electrosurgical generators that may be suitable for use as a source of electrosurgical energy are commercially available under the trademarks FORCE EZ™, FORCE FX™, and FORCE TRIAD™ offered by Covidien Surgical Solutions of Boulder, Colo. Electrosurgical instrument 10 may alternatively be configured as a wireless device or battery-powered.

As shown in FIG. 1, the end-effector assembly 100 is rotatable about a longitudinal axis "A-A" through rotation, either manually or otherwise, of the rotatable assembly 80. Rotatable assembly 80 generally includes two halves (not shown), which, when assembled about the shaft 12, form a generally circular rotatable member 82. Rotatable assembly 80, or portions thereof, may be configured to house a drive assembly (not shown) or components thereof. Examples of rotatable assembly embodiments and drive assembly embodiments of the electrosurgical instrument 10 are described in the above-mentioned, commonly-assigned U.S. Pat. Nos. 7,150,097, 7,156,846, 7,597,693 and 7,771,425.

Handle assembly 30 includes a fixed handle 50 and a movable handle 40. In some embodiments, the fixed handle 50 is integrally associated with the housing 60, and the movable handle 40 is selectively movable relative to the fixed handle 50. Movable handle 40 of the handle assembly 30 is ultimately connected to the drive assembly (not shown). The shape and size of the handle assembly 30 may be varied from the configuration depicted in FIG. 1.

As can be appreciated, applying force to move the movable handle 40 toward the fixed handle 50 pulls a drive sleeve proximally to impart movement to the first and second jaw members 110 and 120 from an open position, wherein the first and second jaw members 110 and 120 are disposed in spaced relation relative to one another, to a clamping or closed position, wherein the first and second jaw members 110 and 120 cooperate to grasp tissue therebetween. Examples of handle assembly embodiments of the electrosurgical instrument 10 are described in the above-mentioned, commonly-assigned U.S. Pat. Nos. 7,150,097, 7,156,846, 7,597,693 and 7,771,425.

Electrosurgical instrument 10 includes a switch 200 configured to permit the user to selectively activate the instrument 10 in a variety of different orientations, i.e., multi-oriented activation. As can be appreciated, this simplifies activation. When the switch 200 is depressed, electrosurgical energy is transferred through one or more electrical leads to the first and second jaw members 110 and 120. Although FIG. 1 depicts the switch 200 disposed at the proximal end of the housing assembly 60, the switch 200 may be disposed on another part of the instrument 10 (e.g., fixed handle 50, rotatable member 82, etc.) or another location on the housing assembly 60.

FIG. 2 shows an electrosurgical instrument 20 for use with various surgical procedures, e.g., vessel sealing with bipolar spot heating, in accordance with the present disclosure. Electrosurgical instrument 20 includes the housing 60, the handle assembly 30, the shaft 12, and the end-effector assembly 100, and is similar to the device 10 shown in FIG. 1. Accordingly, only those features unique to electrosurgical instrument 20 are described in detail.

Electrosurgical instrument 20 includes four transmission lines 231, 232, 241 and 242 coupled between the end-effector assembly 100 and the cable 90, which further operably connect the electrosurgical instrument 20 to the electrosurgical power generating source 28. Housing 60 and the handle assembly 30 may be adapted to provide various configurations of electrical connections between the end-effector assembly 100, or components thereof, the switch 200 and/or the cable 90.

As shown in FIG. 2, the first sealing plate 112 of the end-effector assembly 100 is connected via a first transmission line 231 to the cable 90. The second sealing plate 122 is connected via a second transmission line 232 to the cable 90. The first bipolar electrode 114 is connected via a third transmission line 241 to the cable 90. The second bipolar electrode 124 is connected via a fourth transmission line 242 to the cable 90. This configuration enables a controller, logic, circuitry, and/or code integrated with the electrosurgical power generating source 28 (or other component of an electrosurgical system) to select between the first bipolar electrode 114, the second bipolar electrode 124, the first sealing plate 112, and/or the second sealing plate 122. Electrosurgical power generating source 28 may be configured to activate the first sealing plate 112, the second sealing plate 122, the first bipolar electrode 114, and the second bipolar electrode 124, in single or paired configurations.

FIG. 3 shows an electrosurgical instrument 30 for use with various surgical procedures, e.g., vessel sealing with bipolar spot heating, in accordance with the present disclosure. Electrosurgical instrument 30 includes the housing 60, the handle assembly 30, the shaft 12, and the end-effector assembly 100 shown in FIG. 1. Electrosurgical instrument 30 is similar to the device 10 shown in FIG. 1, except for the switch assembly 301 and the electrical connections thereto, and further description of like elements is omitted in the interests of brevity.

Electrosurgical instrument 30 includes a user interface 370 including a switch assembly 301. Switch assembly 301 includes a user-actuable button "B" configured to allow finger actuation of an actuator (not shown) or any suitable device that generally fulfills the purpose of connecting and disconnecting transmission lines. Electrosurgical instrument 30 includes first, second, third and fourth transmission lines 331, 332, 341 and 342, respectively, coupled between the end-effector assembly 100 and the switch assembly 301. Although FIG. 3 depicts the switch assembly 301 disposed at the proximal end of the housing assembly 60, the switch assembly 301, and/or other component of the user interface 370, e.g., the switch 200, may be disposed on another part of the instrument 30 or another location on the housing assembly 60.

As shown in FIG. 3, the first, second, third and fourth transmission lines 331, 332, 341 and 342 are disposed, in part, within the housing 60 and extend outwardly from the proximal end of the housing 60, passing throughout the length of the shaft 12, to the end-effector assembly 100. The first and second transmission lines 331 and 332 operably connect the first and second sealing plates 112 and 122, respectively, to the switch assembly 301. The third and fourth transmission lines 341 and 342 operably connect the first and second bipolar electrodes 114 and 124, respectively, to the switch assembly 301. A fifth transmission line 391 and a sixth transmission line 392 are disposed, in part, within the fixed handle 50 and configured to connect the switch assembly 301 to the cable 90, which further operably connects the electrosurgical instrument 30 to the electrosurgical power generating source 28. It is to be understood that the dashed lines indicative of electrical connections (e.g., electrical conductors) between various components of the electrosurgical instrument 30 shown in FIG. 3 are merely illustrative and non-limiting examples of electrical connections, and that electrosurgical instrument embodiments of the present disclosure may utilize many different configurations of electrical connections, some with fewer, or additional, electrical connections than depicted in FIG. 3.

Figure 4:
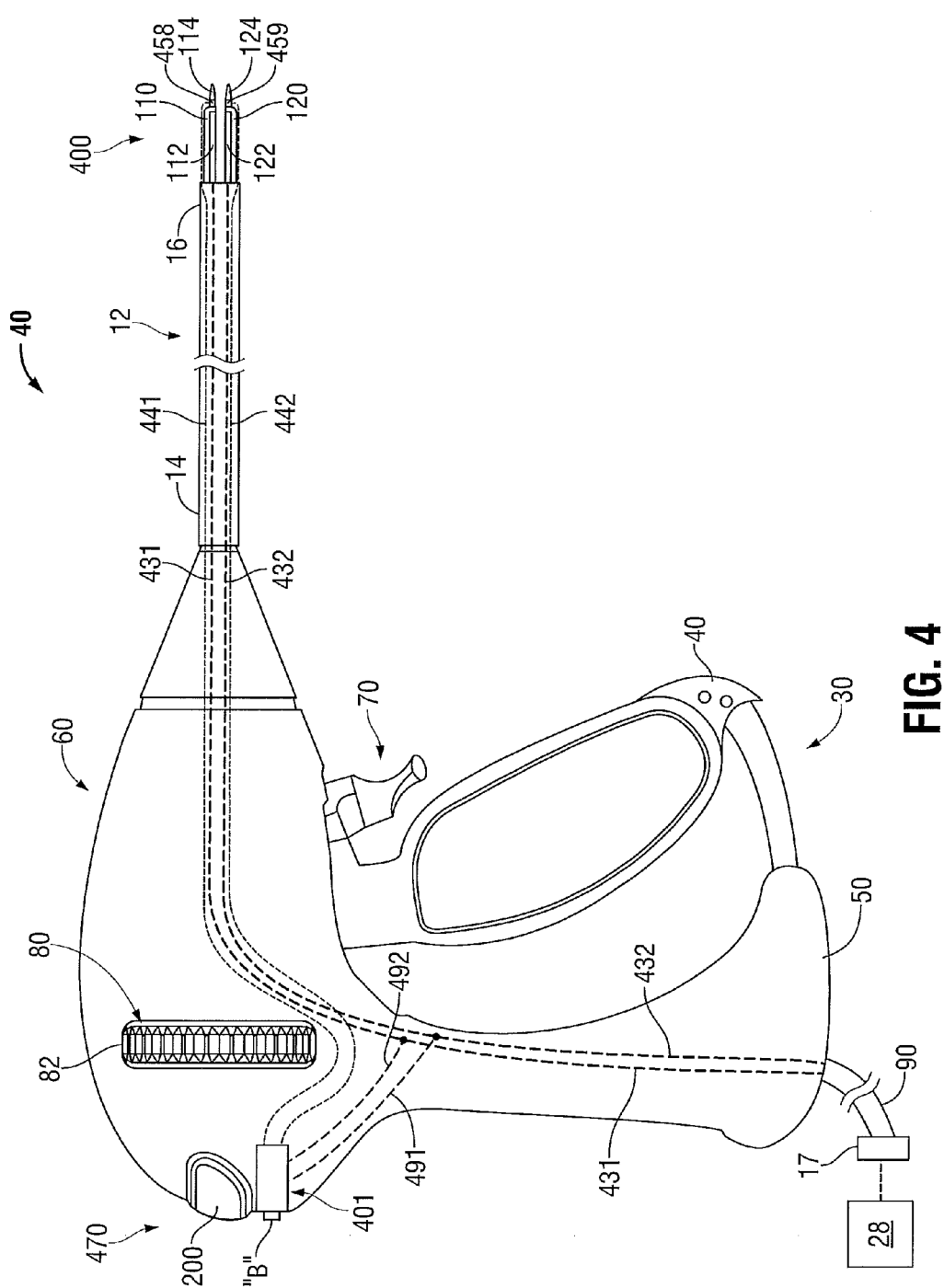
FIG. 4 is a schematic view of an electrosurgical instrument including an end-effector assembly that includes electrically-conductive, tissue-engaging surfaces and bipolar electrodes, a semiconductor switch disposed proximate to each bipolar electrode, and a switch assembly operably coupled to the semiconductor switches in accordance with an embodiment of the present disclosure.

FIG. 4 shows an electrosurgical instrument 40 for use with various surgical procedures, e.g., vessel sealing with bipolar spot heating, in accordance with an embodiment of the present disclosure. Electrosurgical instrument 40 includes an end-effector assembly 400 including the first and second jaw members 110 and 120, the first and sealing plates 112 and 122, and the first and second bipolar electrodes 114 and 124 of the end-effector assembly 100 shown in FIG. 1. Electrosurgical instrument 40 includes first and second semiconductor switches 458 and 459.

Electrosurgical instrument 40 includes a user interface 470 including a switch assembly 401. Switch assembly 401 includes a user-actuable button "B" configured to allow finger actuation of an actuator (not shown) or any suitable device that generally fulfills the purpose of connecting and disconnecting transmission lines. Switch assembly 401 is operably coupled to the first and second semiconductor switches 458 and 459.

Electrosurgical instrument 40 includes first, second, third and fourth transmission lines 431, 432, 441 and 442, respectively, coupled to the end-effector assembly 400. As shown in FIG. 4, the first and second transmission lines 431 and 432 are disposed, in part, within the housing 60 and extend outwardly therefrom, passing throughout the length of the shaft 12, to the end-effector assembly 400. The first and second transmission lines 431 and 432 operably connect the first and second sealing plates 112 and 122 to the switch 401. The first and second bipolar electrodes 114 and 124 are connected to the first and sealing plates 112 and 122 through the first and second semiconductor switches 458 and 459, respectively. When a small bias voltage or current is applied the first and second semiconductor switches 458 and 459 become conducting or non-conducting. In accordance with various embodiments of the present disclosure, a smaller diameter pair of electrical conductors (e.g., transmission lines 431, 432) which do not conduct the therapeutic current (rather, only conduct the bias current) can be connected to a switch disposed either in the instrument (e.g., switch assembly 401) or in the electrosurgical power generating source 28 in order to select between vessel sealing (e.g., sealing plates 112, 122) and bipolar spot heating (e.g., bipolar electrodes 114, 124).

In some embodiments, fifth and sixth transmission lines 491 and 492, respectively, disposed in part within the housing 60 and in part within the fixed handle 50 connect the switch assembly 301 to the first and second transmission lines 431 and 432 extending from the cable 90, which further operably connects the electrosurgical instrument 40 to the electrosurgical power generating source 28. In contrast to the electrosurgical instruments 20 and 30 shown in FIG. 2 and FIG. 3, respectively, which make use of a second pair of electrical conductors, e.g., wires, between the instrument and the electrosurgical power generating source 28 (e.g., a length of several meters), in the case of the electrosurgical instrument 40 shown in FIG. 4, the need for the second pair of electrical conductors from the electrosurgical power generating source 28 is eliminated, which allows for the use of a less expensive cable. In the electrosurgical instrument 40, the smaller diameter pair of electrical conductors 441, 442 extending through the instrument shaft 12 may allow for the use of a smaller diameter shaft, which may allow for smaller incisions, enhanced maneuverability, and/or increased visibility.

The first semiconductor switch 458 and the second semiconductor switch 459 are connected via the third and fourth transmission lines 441 and 442, respectively, to the switch assembly 401. In some embodiments, as shown in FIG. 4, the first semiconductor switch 458 is disposed proximate to the first bipolar electrode 114, and the second semiconductor switch 459 is disposed proximate to the second bipolar electrode 124.

Figure 6:
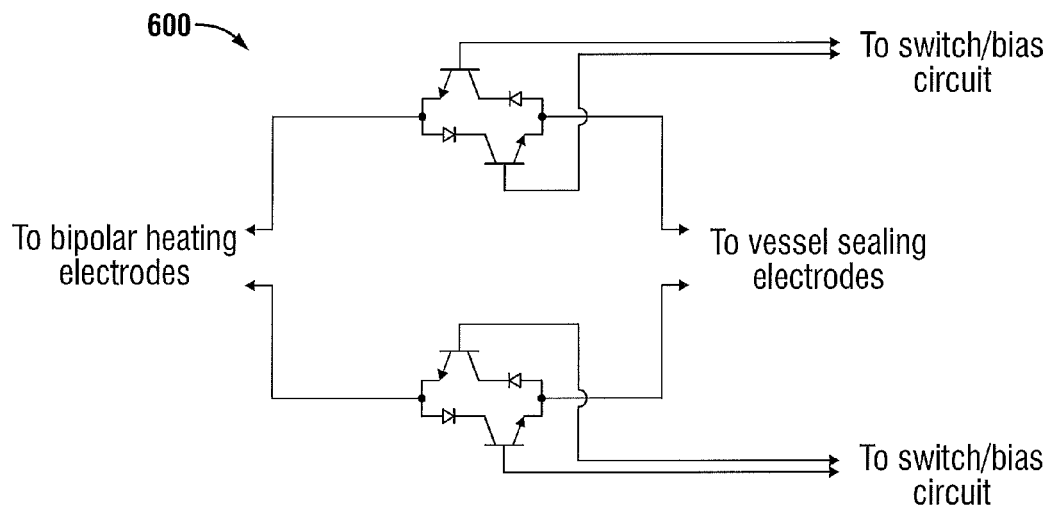
FIG. 6 is a circuit diagram schematically illustrating a four-quadrant semiconductor switch.
Figure 7:
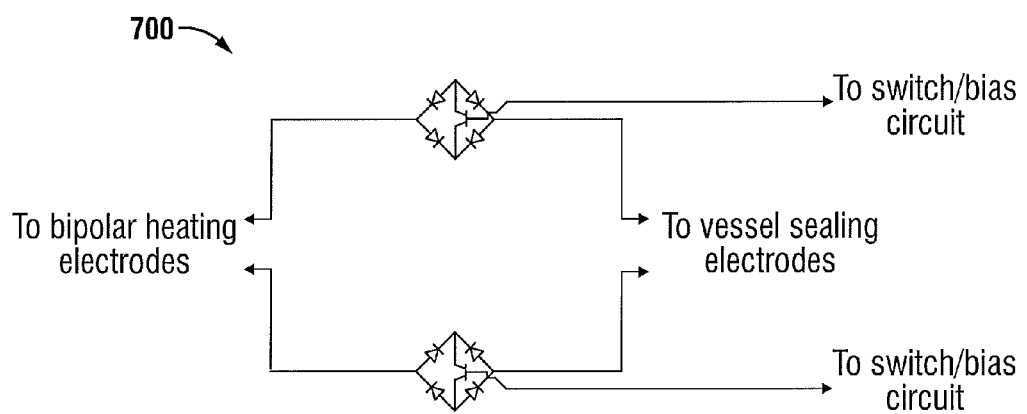
FIG. 7 is a circuit diagram schematically illustrating a four-quadrant semiconductor switch.

In some embodiments, the first and second semiconductor switches 458 and 459 are realized using four-quadrant semiconductor switch configurations. Some examples of four-quadrant semiconductor switch configurations that may be suitable for the first semiconductor switch 458 and/or the second semiconductor switch 459 are shown in FIGS. 6 and 7. In some embodiments, the transistor(s) used may be field-effect transistors, rather than bipolar junction transistors. In other embodiments, the semiconductor junction is biased from non-conducting to conducting using a source of light, rather than electric charge, and may include a light activated SCR (LASCR) or other light-sensitive transistor(s) or thyristor(s). Semiconductor junctions may be combined in an a variety of ways to realize a four-quadrant switch suitable for the first semiconductor switch 458 and/or the second semiconductor switch 459.

Figure 5:
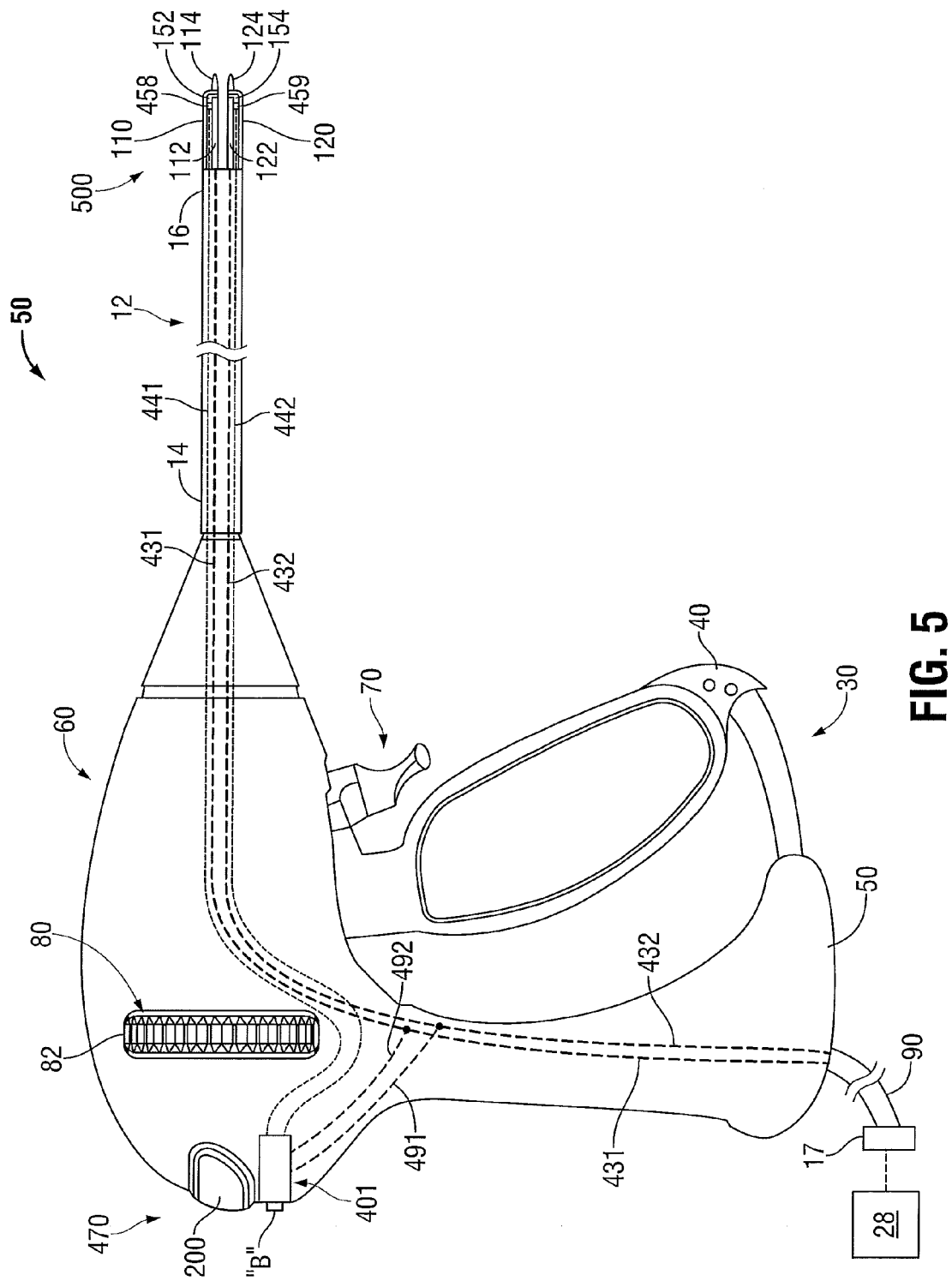
FIG. 5 is a schematic view of an electrosurgical instrument including an end-effector assembly, a semiconductor switch disposed within an non-electrically conductive member disposed between each jaw member and electrically-conductive, tissue-engaging surface of the end-effector assembly, and a switch assembly operably coupled to the semiconductor switches in accordance with an embodiment of the present disclosure.

FIG. 5 shows an electrosurgical instrument 50 including an end-effector assembly 500. End-effector assembly 500 is similar to the device 40 shown in FIG. 4, except for the first and second non-electrically conductive members 152 and 154 and the location of the first and second semiconductor switches 458 and 459, and further description of like elements is omitted in the interests of brevity.

End-effector assembly 500 includes a first non-electrically conductive member 152 disposed between the first jaw member 110 and the first electrically-conductive, tissue-engaging surface 112, a second non-electrically conductive member 154 disposed between the second jaw member 120 and the second electrically-conductive, tissue-engaging surface 114. The first bipolar electrode 114 is coupled to the distal end of the first jaw member 110, and the second bipolar electrode 124 is coupled to the distal end of the second jaw member 120.

The first semiconductor switch 458 is disposed at least in part within the first non-electrically conductive member 152. The second semiconductor switch 459 is disposed at least in part within the second non-electrically conductive member 154.

FIG. 6 shows a circuit diagram schematically illustrating a four-quadrant switch. In FIG. 6, each semiconductor junction is shown as two bipolar junction transistors and two diodes, comprising a four-quadrant switch (e.g., a combination of semiconductor junctions which can conduct either positive or negative current as well as block either positive or negative voltage). FIG. 7 is a circuit diagram schematically illustrating a four-quadrant switch. In the embodiment shown in FIG. 7, each four-quadrant switch is realized using four diodes and one transistor.

The above-described electrosurgical instrument embodiments including any combination of features of the presently-disclosed end-effector configurations adding switchable bipolar electrodes to the instrument using four-quadrant semiconductor switches may be used in connection with jaw members, sealing plates, and bipolar electrodes of varied geometries, e.g., lengths and curvatures, such that variously-configured jaw members, sealing plates, and bipolar electrodes may be fabricated and assembled into various end-effector configurations that include four-quadrant semiconductor switches in the instrument tip, e.g., depending upon the design of specialized electrosurgical instruments.

The above-described electrosurgical instruments with an end-effector assembly including electrically-conductive, tissue-engaging surfaces and switchable bipolar electrodes may be suitable for sealing, cauterizing, coagulating/desiccating and/or cutting vessels and vascular tissue. The above-described electrosurgical instruments may be suitable for utilization in endoscopic surgical procedures and/or suitable for utilization in open surgical applications.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. An electrosurgical instrument, comprising:
    a housing;
    an elongated shaft including a distal end and a proximal end, the proximal end operably associated with the housing;
    an end-effector assembly operably coupled to the distal end of the elongated shaft and including first and second jaw members, each of the first and second jaw members coupled to an electrically-conductive, tissue-engaging surface and a bipolar electrode, at least one of the first and second jaw members movable from a position in spaced relation relative to the other jaw members to at least one subsequent position wherein the electrically-conductive, tissue-engaging surfaces cooperate to grasp tissue therebetween; and
    a four-quadrant semiconductor switch operably coupled to at least one of the electrically-conductive, tissue-engaging surfaces and at least one of the bipolar electrodes, wherein the semiconductor switch is configured to enable user selection between energizing the at least one electrically-conductive, tissue-engaging surface or energizing the at least one bipolar electrode.

2. The electrosurgical instrument of claim 1, wherein the four-quadrant semiconductor switch is disposed proximate to the at least one bipolar electrode.

3. The electrosurgical instrument of claim 1, further comprising a switch assembly associated with the housing, wherein the switch assembly is operably coupled to an electrosurgical power generating source.

4. The electrosurgical instrument of claim 3, wherein the switch assembly is electrically coupled to the four-quadrant semiconductor switch.

5. The electrosurgical instrument of claim 3, further comprising a first pair of electrical conductors configured to connect the electrically-conductive, tissue-engaging surfaces to the switch assembly.

6. The electrosurgical instrument of claim 5, further comprising a second pair of electrical conductors configured to connect the four-quadrant semiconductor switch to the switch assembly.

7. The electrosurgical instrument of claim 6, wherein a diameter of the second pair of electrical conductors is less than a diameter of the first pair of electrical conductors.

8. An electrosurgical instrument, comprising:
    a housing;
    an elongated shaft including a distal end and a proximal end, the proximal end operably associated with the housing;
    an end-effector assembly operably coupled to the distal end of the elongated shaft, the end-effector assembly including:
        a first jaw member;
        a second jaw member;
        a first electrically-conductive, tissue-engaging surface associated with the first jaw member;
        a second electrically-conductive, tissue-engaging surface associated with the second jaw member;
        a first bipolar electrode coupled to a distal end of the first jaw member;
        a second bipolar electrode coupled to a distal end of the second jaw member; and
        a first four-quadrant semiconductor switch operably coupled to the first electrically-conductive, tissue-engaging surface and the first bipolar electrode, wherein the first four-quadrant semiconductor switch is configured to enable user selection between energizing the first electrically-conductive, tissue-engaging surface or energizing the first bipolar electrode.

9. The electrosurgical instrument of claim 8, wherein the first jaw member is movable from a position in spaced relation relative to the second jaw member to at least one subsequent position wherein the first and second electrically-conductive, tissue-engaging surfaces cooperate to grasp tissue therebetween.

10. The electrosurgical instrument of claim 8, wherein the first four-quadrant semiconductor switch is disposed proximate to the first bipolar electrode.

11. The electrosurgical instrument of claim 8, further comprising a first non-electrically conductive member disposed between the first jaw member and the first electrically-conductive, tissue-engaging surface.

12. The electrosurgical instrument of claim 11, wherein the first four-quadrant semiconductor switch is disposed at least in part within the first non-electrically conductive member.

13. The electrosurgical instrument of claim 8, further comprising a switch assembly associated with the housing, wherein the switch assembly is electrically coupled to the first four-quadrant semiconductor switch.

14. The electrosurgical instrument of claim 13, wherein the switch assembly is configured to selectively output a biasing current for biasing the first four-quadrant semiconductor switch.

15. The electrosurgical instrument of claim 13, further comprising a first pair of electrical conductors configured to connect the electrically-conductive, tissue-engaging surfaces to the switch assembly.

16. The electrosurgical instrument of claim 15, further comprising a second pair of electrical conductors configured to connect the first four-quadrant semiconductor switch to the switch assembly, wherein a diameter of the second pair of electrical conductors is less than a diameter of the first pair of electrical conductors.

17. The electrosurgical instrument of claim 8, further comprising a second non-electrically conductive member disposed between the second jaw member and the second electrically-conductive, tissue-engaging surface.

18. The electrosurgical instrument of claim 17, further comprising a second four-quadrant semiconductor switch, the second four-quadrant semiconductor switch disposed at least in part within the second non-electrically conductive member.

* * * * *